US006605706B1

(12) United States Patent
Gustafsson et al.

(10) Patent No.: US 6,605,706 B1
(45) Date of Patent: Aug. 12, 2003

(54) METHOD FOR PRODUCING A CORRECTLY FOLDED, BIOLOGICAL ACTIVE RECOMBINANT PROTEIN

(75) Inventors: Jan-Gunnar Gustafsson, Uppsala (SE); Johan Öhman, Upplands-Väsby (SE)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 09/051,941

(22) PCT Filed: Nov. 12, 1996

(86) PCT No.: PCT/SE96/01456

§ 371 (c)(1),
(2), (4) Date: Jul. 6, 1998

(87) PCT Pub. No.: WO97/18233

PCT Pub. Date: May 22, 1997

(30) Foreign Application Priority Data

Nov. 13, 1995 (SE) ................................................ 9504019

(51) Int. Cl.[7] .......................... C07K 1/14; C07K 14/46; C12N 15/12; C12N 1/21; C12N 15/00
(52) U.S. Cl. ...................... 530/412; 530/413; 530/414; 530/416; 530/300; 530/350; 530/399; 453/69.1; 453/69.4; 453/69.7; 453/252.3; 453/252.8; 453/320.1
(58) Field of Search .................... 530/412, 416, 530/413, 422, 399, 418, 420, 423, 424, 414, 300, 350; 435/69.1, 69.4, 172.3, 320.1, 252.3, 69.7, 252.8

(56) References Cited

U.S. PATENT DOCUMENTS

| 5,288,931 A | * | 2/1994 | Chang et al. | ............... | 435/69.1 |
| 5,407,810 A | * | 4/1995 | Builder et al. | ............... | 435/69.1 |
| 5,473,049 A | * | 12/1995 | Obermeier et al. | ......... | 530/303 |
| 5,756,672 A | * | 5/1998 | Builder et al. | ............... | 530/350 |

FOREIGN PATENT DOCUMENTS

| EP | 230 869 | * 12/1986 |
| WO | WO 9212993 | 8/1992 |
| WO | WO 9506059 | 3/1995 |
| WO | WO 9506064 | 3/1995 |

OTHER PUBLICATIONS

Harris et al. Protein Purification Methods: A Practical Approach, Sep. 1989, IRL Press, Oxford, UK, pp. 69–70, 81, 151–152, 175.*
Jyh–Ping Chen, Journal of Fermentation and Bioengineering, vol. 70, No. 3, pp. 199–209, 1990.*
Hart et al, *Bio/Technology*, 12:1113–1117 (Nov. 1994).

* cited by examiner

*Primary Examiner*—David S. Romeo
(74) *Attorney, Agent, or Firm*—Dinsmore & Shohl LLP

(57) ABSTRACT

Methods for producing correctly folded biological active recombinant protein or polypeptide comprise the steps of expressing the protein or polypeptide in prokaryotic cells, harvesting the cells, directly solubilizing the cells in a buffer at pH of about 8 to 11 with the chaotropic agent and a reducing agent, and diluting the solution with water and a diluent. The method is conducted in the absence of mechanical disruption of the cells and isolation and washing of refractile bodies.

19 Claims, No Drawings

METHOD FOR PRODUCING A CORRECTLY FOLDED, BIOLOGICAL ACTIVE RECOMBINANT PROTEIN

The present invention relates to a method for producing a correctly folded, biological active recombinant protein or polypeptide, comprising the steps of expression of the protein in prokaryotic cells, harvest of the cells, direct solubilization of the cells in a buffer at pH about 8 to 11 and thereafter dilution with water and a diluent.

The protein or polypeptide is preferably GH, IGF-I or IGF-II.

INTRODUCTION

A general, major problem when recombinant proteins are overproduced in efficient bacterial expression systems is related to the folding of the protein products into their native conformations. Many high level expression systems in *Escherichia coli* result in the production of aggregates of denatured proteins, so called inclusion bodies, which in some cases may be refolded into the wanted native protein. General methods to facilitate and render the refolding effective have been found. One is the use of a class of heat-shock-proteins (HSP) and the other is folding-enzymes. By using HSP, aggregation is avoided and by using the folding enzymes, the speed of refolding is accelerated.

However, not all proteins are susceptible for these methods and other solutions to enhance refolding yields have been suggested. In an article by J D Carlson et al in Biotechnology, Vol 10, January 1992, the use of monoclonal antibodies during protein refolding, to enhance the yield of native protein, especially S-Protein, has been disclosed.

Another suggested method for the recovery of the native protein is solubilization of the inclusion body protein with a denaturant, such as guanidine or urea and if needed a reduction of the disulphide bond. By dilution or dialysis and reoxidation, the protein can be refolded to the native protein.

Successful refolding, without formation of new inclusion bodies, is generally difficult at high concentrations of the recombinant protein. The best yield is generally achieved at concentrations around 20–200 µg/ml. Refolding is therefore considered to be a very expensive production form that demands a cost intensive drug.

However, the yield of a refolding procedure is unpredictable since the protein product often aggregates or gets modified. In addition, for IGF-I and II, the soluble refolded fraction will contain misfolded species and the overall yield of correctly folded growth factor is rather low (Samuelsson, E., et al (1991) Bio/Technology Vol. 9, Page 363).

In order to increase the yield of correctly folded IGF-I different methods have been proposed.

Human insulin-like growth factor I (IGF-I) is a single-chain peptide growth factor of 70 amino acids, originally isolated from serum. IGF-I is positively regulated by growth hormone (GH) and shows mitogenic effects on many cell types. Therefore, IGF-I is thought to mediate many of the growth promoting effects of GH. In the regions of homology, IGF-I and insulin are 49% homologous, including the six cysteine residues, furnishing three disulphide bridges. The three dimensional structure of IGF-I has been modelled based on the x-ray structure of insulin, and this model has recently been confirmed in the disulphide bridge regions by distance constraints obtained by 2-D NMR spectroscopy of IGF-I (for a review on IGF, see: Insulin-like growth factors I and II, Humbel R. E, Eur. J. Biochem 190, 445462,1990).

Human recombinant IGF-I has been produced as a secreted product in both *Escherichia coli* and *Saccharomyces cerevisiae*. In isolated material from both species, IGF-I is found mainly as miss-folded forms with intermolecular disulphides. In addition, in vitro refolding of reduced IGF-I in the presence of oxygen, has demonstrated that native, miss-matched and aggregated IGF-I accumulate, even under dilute refolding conditions.

The refolding yield of recombinant IGF-I was significantly improved by utilising a fused fusion partner, consisting of two IgG-binding domains (ZZ) derived from staphylococcal protein A (Samuelsson, E., et al (1991) Bio/Technology Vol. 9, Page 363). The ZZ fusion partner is used to solubilise misfolded molecules before, during and after reduction and reoxidation. The yield of correctly folded IGF-I is shown to be substantially increased but there is still a significant amount of misfolded IGF.

Patents and patent applications have also described the problem of misfolded IGF and suggested different improvements.

WO 91/02807 (Amgen) (=U.S. Pat. No. 5,158,875) discloses a method for refolding IGF-I in the presence of a fused short positively charged leader sequence, in which amino acids, such as lysine, arginine and histidine are fused at the N-terminus of IGF-I. Inclusion bodies are isolated and solubilized with urea. In WO 93/11240 (Genentech) a method for refolding of insoluble and improperly folded IGF-I is described involving solubilisation of inclusion bodies and refolding in a single buffer system.

U.S. Pat. No. 5,151,501 (American Cyanamid) discloses a process for solubilization and naturation of somatropins (Growth hormones) by dispersing somatropin refracfile bodies in a solution containing sulfolane and thereafter dilution.

WO 9319084 (Synergen) discloses a method for producing active IGF-I is claimed, comprising the steps of expressing in prokaryotic cell, adding a first reducing agent, adding denaturing agent (e.g. urea), adding oxidizing agent (e.g. oxidized gluthatione or cystein) and adding a second reducing agent (e.g. DTT, cystein etc.). Met-IGF-I is expressed.

WO 9506064 discloses a process for increasing the yield of correct refolding of a polypeptide and in which a copper or manganese salt are present during the refolding step and WO 9506059 (Genentech) discloses a method for isolation of cells by adding a phase-forming species to form mutilple aqueous phase.

SUMMARY OF THE INVENTION

We have now invented a novel, simplified method for the production of correctly folded biological active recombinant protein or polypeptide.

Especially we refer to recombinant IGF-I after expression of Z- IGF-I. Reference is here given to EP 230 869, especially the examples.

With *Escherichia coli* expressing the hybrid protein Z-IGF-I, we have achieved very high expression levels (up to 15 g/l fermentation).

Although the method here is described with IGF-I as the preferred polypeptide, it can also be used for recombinant preparation of other polypeptides, when misfolded species and the overall yield of correctly folded polypeptide is rather low.

With our claimed method we can avoid the steps of mechanical disruption of the cells and the isolation and washing of refractile bodies.

Our process is easier than the earlier described and gives a good yield.

The invention relates to a method for producing a correctly folded, biological active recombinant protein or polypeptide, comprising the steps of a) expression of the protein in prokaryotic cells,
b) harvest of the cells),
c) direct solubilization of the cells in a buffer at pH about 8 to 11, preferably about 8, with a chaotropic agent and a reducing agent, and
d) dilution with water and a diluent.

The protein could e.g. be IGF-I, IGF-II or GH.

When the protein is IGF-I the method preferably comprises the steps of a) expression of an IGF-I-fusion protein in prokaryotic cell system, preferably *E Coli,*
b) harvest of the cells),
c) direct solubilization of the cells in a buffer at pH 8 to 11, preferably about 8, with a chaotropic agent and a reducing agents,
d) dilution with water and a diluent,
e) addition of a cleaving agent, and
f) purification to produce the biological active IGF-I.

The IGF-I-fusion protein is preferably a hybrid Z-IGF-I. The buffer in step c) could be e.g. Tris (Tris [hydroxymethyl]aminomethane hydrochloride) or glycine.

The chaotropic agent in step c) is preferably guanidine or urea and guanidine could be used in a concentration of 3–7M, preferably 5M.

The reducing agent in step c) could be e.g. DTT (DL-Dithiothreito) or cysteine and the diluent in step d) could be ethanol.

After step d), pH is preferably reduced below pH 6 and more preferably to pH 3 or below.

For the preparation of IGF-I pH is preferably reduced to pH 3 or below between steps d) and e).

A concentration step and a buffer exchange between steps d) and e), in which chromatography and/or ion-exchange preferably is used is also claimed.

The cleaving agent in step e) in the preparation of IGF-I could be hydroxylamine, an enzyme or any other cleaving agent.

The purification steps for the preparation of the pure protein or polypeptide include e.g. cation exchange, RP-HPLC and/or hydrophobic interaction Chromatography (HIC).

When IGF-I is produced as Z-IGF-I, IGF-I has a better solubility, which means that we can have a higher concentration of reduced IGF-I in solution, giving a high amount of right folded IGF-I which is of most importance for an industrial method for the production of IGF-I.

EXAMPLES

The recombinant human IGF-I (rhIGF-I) used in the experiments was produced in *E Coli* according to the method described in EP 230 869, example VIII (but in a fermentor) including growing at 37° C. for 20 hours.

Example 1

Solubilization

The cells were harvested after fermentation by centrifugation or cross flow filtration.

Thereafter the cells were dissolved in:

13 L cell solution, wet weight 498 g/L
5 mol/L guanidine-hydrochloride
97 mmol/L Tris-base
159 mmol/L Tris-HC1
2 mmol/L ethylene-dinitro-tetraacetic acid-disodiumsalt-dihydrate (EDTA)
4 mmol/L dithiothreitol (DDT)
Total volume: 16.9 L The pH was kept at 8.1, the solubilization was run for 3 hours under stirring at 150° C.

Refolding

The solubilization solution was diluted with 33.8 L 22.5% ethanol solution, dilution factor 3.

The pH was kept at 8.1, under stirring at 15° C.

The refolding was stopped after 20 hours by addition of concentrated hydrochloric acid until the pH of the solution was <3.1.

RP-HPLC analysis of the concentration of Z-IGF-I in the refolding solution gave correctly folded 3.249 g ZIGF-I/L.

Example 2

Solubilization

The cells were harvested after fermentation by centrifugation or cross flow filtration.

Thereafter the cells were dissolved in:

154 mL cell solution, wet weight 450 g/L
4.5 mol/L guanidine-hydrochloride
400 mmol/L glycine
0.2% Tween 20
0.2 mmol/L ethylene-dinitro-tetraacetic acid-disodiumsalt-dihydrate (EDTA)
3 mmol/L dithiothreitol (DDT)
Total volume: 200 mL The pH was kept at 10.0, the solubilization was run for 3 hours under stirring at room temperature.

Refolding

The solubilization solution was diluted with 125 mL ethanol, 400 mL water, 66.8 g guanidine-hydrochloride, dilution factor 4.

The pH was kept at 10.0, under stirring at room temperature.

The refolding was stopped after 20 hours by addition of concentrated hydrochloric acid until the pH of the solution was <3.1.

RP-HPLC analysis of the concentration of Z-IGF-I in the refolding solution gave correctly folded 1.38 g ZIGF-I/L.

Example 3

Solubilization

The cells were harvested after fermentation by centrifugation or cross flow filtration.

Thereafter the cells were dissolved in:

900 mL cell solution, wet weight 720 g/L
6 mol/L guanidine-hydrochloride
97 mmol/L Tris-base
159 mmol/L Tris-HC1
2 mmol/L ethylene-dinitro-tetraacetic acid-disodiumsalt-dihydrate (EDTA)
3 mmol/L dithiothreitol (DDT)
Total volume: 1.17 L The pH was kept at 8.0, the solubilization was run for 3 hours under stirring at 15° C.

Refolding

The solubilization solution was diluted with 547 mL ethanol 1786 mL water, dilution factor 3.

Total volume: 3.6 L

The pH was kept at 8.1, under stirring at 15° C.

The refolding was stopped after 21 hours by addition of concentrated hydrochloric acid until the pH of the solution was <3.1.

RP-HPLC analysis of the concentration gave correctly folded 1.32 g Z-IGF-I/L.

Yield

Solubilization: 74% (of ZIGF-I from the fermentor)

Total, solubilization and refolding: 41%

Finally purified IGF-I was shown to have biological activity in e.g. chick embryo femore and RRA (Radio Receptor Assay).

Example 4

First Purification Step

A solution from the refolding step was diluted with WFI (Water for Injection), dilution factor 3 and clarified on a cross flow membrane before applied on a cation exchanger (Pharmacia Biotech BPG 200/500, SP-Sepharose FF, 9.5 Liters, 0.33 m bed high).

The following buffers were used:

| Step | Buffer | pH |
|---|---|---|
| Equilibration | 100 mM Citric acid/di-Na hydrogen phosphate | 3.0 |
| Wash 1 | 50 mM Citric acid/di-Na hydrogen phosphate | 2.9 |
| Wash 2 | 100 mM di-Na hydrogen- and Na-dihydrogen phosphate | 5.9 |
| Elution | 100 mM Na hydrogen phosphate | 7.5 |
| Regeneration | 500 mM NaOH | |
| Sanitation | 100 mM NaOH | |

The column was washed with 1 Column volume (CV) WFI, the column was treated with 3 CV of Equilibration buffer and the sample was hereafter applied on the column.

The column was first washed with 3 CV of Wash 1 buffer and thereafter with 4 CV Wash 2 buffer.

The product was eluted with 5 CV of elution buffer and the column treated with 2 CV of Regeneration buffer and 2 CV of Sanitation buffer.

According to RP-HPLC the yield over the purification step was 98% correctly folded IGF-I.

Example 5

Cleavage Step

After the first purification step on a cation ion exchange column, the cleavage of Z from IGF-I was performed.

To a vessel was added: 40.0 Liters from the cation ion exchanger pool, 1428 grams Sodium diphosphate and 4.0 Liters Hydrozylamine, 50% sol.

The pH was adjusted to 9.55 (with NaOH) and the temperature was kept at 40° C.

After 3 hours the reaction was stopped by lowering the temperature to 25° C. and adding 40.0 Liters concentrated Acetic acid (HAc) and 160 Liters WFI.

The pH was adjusted to 3.30.

According to RP-HPLC the yield over this step was 84% of correctly folded, non oxidized IGF-I.

Example 6

Cleavage Step

After the first purification step on a cation ion exchange column, the cleavage of Z from IGF-I was performed.

To a vessel was added: 18.6 Liters from the cation ion exchange pool, 664 grams Sodium diphosphate and 2.17 Liters Hydrozylamine, 50% sol.

The pH was adjusted to 9.5 (with HAc) and the temperature was kept at 40° C.

After 3 hours the reaction was stopped by lowering the temperature to 25° C. and adding 22.3 Liters concentrated HAc and 93 Liters WFI.

The pH was adjusted to 3.35.

According to RP-HPLC the yield over this step was 61% of correctly folded, non oxidized IGF-I.

What is claimed is:

1. A method for producing a correctly folded, biologically active recombinant protein or polypeptide, comprising the steps of
    a) expressing the protein or polypeptide in prokaryotic cells,
    b) after step a), harvesting the cells by a process comprising centrifugation or cross flow filtration,
    c) after step b), directly solubilizing the cells in a buffer at pH of about 8 to 11 with a chaotropic agent and a reducing agent to form a solution, and
    d) after step c), diluting the solution with water and a diluent, thereby obtaining the correctly folded, biologically active recombinant protein or polypeptide, the method being conducted in the absence of mechanical disruption of the cells and in the absence of isolation and washing of refractile bodies from within the cells.
2. A method according to claim 1. wherein the protein is IGF-I, IGF-II or GH.
3. A method according to claim 1, wherein the protein is IGF-I and comprising the steps of
    a) expressing an IGF-I fusion protein in a prokaryotic cell system,
    b) after step a), harvesting the cells by a process comprising centrifugation or cross flow filtration,
    c) after step b), directly solubilizing the cells in a buffer at pH of 8 to 11 with a chaotropic agent and a reducing agent to form a solution,
    d) after step c), diluting the solution with water and a diluent, thereby obtaining the correctly folded, biologically active recombinant protein or polypeptide,
    e) adding an agent for cleaving IgG binding domain from IGF-I, and
    f) purifying the IGF-I product of step e) to produce the biologically active IGF-I.
4. Method according to claim 1, wherein the protein is hybrid Z-IGF-I.
5. Method according to claim 1, wherein the buffer in step c) comprises Tris or glycine.
6. Method according to claim 1, wherein the pH in step c) is about 8.
7. Method according to claim 1, wherein the chaotropic agent in step c) comprises guanidine or urea.
8. Method according to claim 1, wherein the reducing agent in step c) comprises DTT or cysteine.

9. Method according to claim 1, wherein the diluent in step d) comprises ethanol.

10. Method according to claim 1, wherein the pH is reduced after step d).

11. Method according to claim 3, wherein the pH is reduced to a pH of not greater than 3 between steps d) and e).

12. Method according to claim 3, further comprising a concentration step and a buffer exchange between steps d) and e).

13. Method according to claim 3, wherein the cleaving agent in step e) comprises hydroxylamine.

14. A method according to claim 3, wherein the cell system comprises *E. Coli*.

15. Method according to claim 7, wherein the chaotropic agent comprises guanidine in a concentration of 3–7M.

16. A method according to claim 10, wherein the pH is reduced after step d) to a pH below 6.

17. A method according to claim 10, wherein the pH is reduced after step d) to a pH not greater than 3.

18. Method according to claim 12, wherein the concentration step employs at least one of chromatography and ion-exchange.

19. Method according to claim 18, wherein the purification step f) includes at least one of cation exchange, RP-HPLC and hydrophobic interaction Chromatography (HIC).

* * * * *